United States Patent [19]

Peterson

[11] Patent Number: 5,447,519
[45] Date of Patent: Sep. 5, 1995

[54] METHOD AND APPARATUS FOR DISCRIMINATION OF MONOMORPHIC AND POLYMORPHIC ARRHYTHMIAS AND FOR TREATMENT THEREOF

[75] Inventor: David K. Peterson, Mounds View, Minn.

[73] Assignee: Medtronic, Inc., Minneapolis, Minn.

[21] Appl. No.: 206,486

[22] Filed: Mar. 19, 1994

[51] Int. Cl.6 ............................................. A61N 1/39
[52] U.S. Cl. ......................................... 607/5; 607/4; 128/705; 364/413.06
[58] Field of Search ................. 607/4, 5, 14; 128/702, 128/705, 696; 364/413.06

[56] References Cited

U.S. PATENT DOCUMENTS

| | | | |
|---|---|---|---|
| 3,937,226 | 2/1976 | Funke | 128/419 D |
| 4,088,140 | 5/1978 | Rockland et al. | 128/419 PG |
| 4,354,497 | 10/1982 | Kahn | 128/419 D |
| 4,375,817 | 3/1983 | Engle et al. | 128/419 D |
| 4,384,585 | 5/1983 | Zipes | 128/419 D |
| 4,548,209 | 10/1985 | Wielders et al. | 128/419 D |
| 4,577,633 | 3/1986 | Berkovits et al. | 128/419 PG |
| 4,577,634 | 3/1986 | Gessman | 128/419 PG |
| 4,587,970 | 5/1986 | Holley et al. | 128/419 PG |
| 4,693,253 | 9/1987 | Adams | 128/419 D |
| 4,712,554 | 12/1987 | Garson, Jr. | 128/419 PG |
| 4,726,380 | 2/1988 | Vollmann et al. | 128/419 PG |
| 4,754,753 | 7/1988 | King | 128/699 |
| 4,790,317 | 12/1988 | Davies | 128/419 D |
| 4,799,493 | 1/1989 | DuFault | 128/705 |
| 4,800,883 | 1/1989 | Winstrom | 128/419 D |

(List continued on next page.)

OTHER PUBLICATIONS

DuFault et al., "Dual Lead Fibrillation Detection for Implantable Defibrillators via LMS Algorithm" *Computers in Cardiology*, 10-7-10, 1986, Boston, Mass, IEEE Computer Soc. Press, 163-6.

Mercando, et al., "Measurement of Differences in Timing and Sequence Between Two Ventricular Electrodes as a Means of Tachycardia Differentiation", *PACE*, vol. 9, Nov.-Dec. 1986 Part II, 1069-78.

Olson, et al., "Onset and Stability for Ventricular Tachyarrhythmia Detection in an Implantable Pacer-Cardioverter-Defibrillator", *Computers in Cardiology*, Oct. 7-10, 1986, 167-170.

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

An implantable cardioverter/defibrillator system provided with method and apparatus for discrimination between monomorphic arrhythmias, e.g. ventricular tachycardia from polymorphic arrhythmias, e.g. ventricular fibrillation. A fiducial point of each successive QRS complex is detected prompting the storage of sampled and digitized waveform data within a timing window bridging the point in time of fiducial point detection. Stored sets of such sampled wave shape data are compared data point to data point resulting in a sampled morphology index value for each compared set. The magnitude of the sampled morphology index value or a series such index values are analyzed to determine the presence of a single or a progression of beat-to-beat waveform changes indicative of a polymorphic single transition or progression of QRS complexes from monomorphic to polymorphic waveforms indicative of an arrhythmia that should be treated with aggressive cardioversion/defibrillation therapies. The system is preferably provided with a closely spaced and widely spaced pairs of electrodes for sensing each QRS complex of the patient's electrocardiogram. The closely spaced electrode pair is coupled to sense detect circuitry for identifying a predetermined fiducial point in the electrical signal associated with a ventricular depolarization and to counting and comparison circuitry for developing rate and onset data. The widely spaced pair of electrodes is coupled to sense and digitizing circuitry for developing the sampled waveform amplitude data from which the morphology index values are derived.

43 Claims, 6 Drawing Sheets

U.S. PATENT DOCUMENTS

| | | | |
|---|---|---|---|
| 4,819,643 | 4/1989 | Menken | 128/419 PG |
| 4,830,006 | 5/1989 | Haluska et al. | 128/419 PG |
| 4,880,004 | 11/1989 | Baker, Jr. et al. | 128/419 PG |
| 4,880,005 | 11/1989 | Pless et al. | 128/419 PG |
| 4,949,719 | 8/1990 | Pless et al. | 128/419 D |
| 4,949,730 | 8/1990 | Cobben et al. | 128/775 |
| 4,953,551 | 9/1990 | Mehra et al. | 128/419 D |
| 5,086,772 | 2/1992 | Larnard et al. | 128/419 D |
| 5,117,824 | 6/1992 | Keimel et al. | 128/419 D |
| 5,163,427 | 11/1992 | Keimel | 128/419 D |
| 5,178,154 | 1/1993 | Ackmann et al. | 128/734 |
| 5,188,105 | 2/1993 | Keimel | 128/419 D |
| 5,193,535 | 3/1993 | Bardy et al. | |
| 5,366,487 | 11/1994 | Adams et al. | 128/705 |

METHOD AND APPARATUS FOR
DISCRIMINATION OF MONOMORPHIC AND
POLYMORPHIC ARRHYTHMIAS AND FOR
TREATMENT THEREOF

BACKGROUND OF THE INVENTION

1. Field of the Invention

This invention relates to detection and discrimination between cardiac arrhythmias and the delivery of appropriate anti-arrhythmia therapies, and more particularly to the discrimination between monomorphic arrhythmias, e.g. most forms of tachycardia, from polymorphic arrhythmias, e.g. fibrillation and certain tachycardia, particularly in an implantable cardioverter/defibrillator.

2. Background Art

By way of definition, in the field of automatic implantable arrhythmia control devices, the term "cardioversion" or "cardioverter" refers to the process of and device for discharging relatively high energy electrical pulses into or across cardiac tissue to arrest a life threatening tachyarrhythmia. Cardioversion pulses may or may not be synchronized with a cardiac depolarization or rhythm and may be applied to arrest a ventricular tachycardia with a lower range energy pulse of around 1–15 Joules or ventricular fibrillation with a medium to high energy pulse of 7–40 Joules, nominally. The arrest of ventricular fibrillation by such pulses is referred to as "defibrillation", a form of cardioversion, and "defibrillators" have been characterized as a form of cardioverter. In the following description and claims, it is to be assumed that these terms are interchangeable, and that use of one term is inclusive of the other device or operation, unless specific distinctions are drawn between them in the context of the use.

Atrial and ventricular fibrillation are characterized by chaotic electrical activity which presents highly variable depolarization wavefronts which are propagated in directions which differ from those seen during normal sinus rhythm. Moreover, the waveforms of successive depolarization wavefronts, as detected across an electrode pair, are irregular in amplitude and hence in appearance when viewed on an electrocardiogram or display and are characterized as "polymorphic". Ventricular fibrillation is highly polymorphic, particularly at onset and during the initial phase before cardiac activity diminishes.

More rhythmic tachycardias present a more regular or monomorphic waveform appearance, although certain ventricular tachycardias appear to be polymorphic, particularly from one heart beat to the next. Ventricular tachycardia may result from reentry conduction through diseased tissue, which results in depolarization wavefronts, also typically propagated in directions which differ from those seen during normal sinus rhythm.

Detection of the occurrence of depolarization wavefronts having directions of propagation which differ from those seen in normal sinus rhythm has been used in various ways in devices intended to detect or confirm the presence of ventricular tachycardia or fibrillation.

For example, U.S. Pat. Nos. 3,937,266, 4,088,140 and 4,354,497 describe systems intended to distinguish abnormal ventricular depolarization wavefronts from depolarization wavefronts which originate in the HIS bundle, Purkinje fiber system. These devices employ a multitude of spaced electrodes coupled to sense amplifiers and attempt to use the relative arrival times of the wavefronts at the various electrodes to detect the occurrence of abnormal conduction.

U.S. Pat. No. 4,754,753 presents a method and apparatus for sensing the probable onset of ventricular fibrillation or pathologic tachyarrhythmias by observing the direction of the depolarization wavefront to predict the onset of harmful ventricular tachyarrhythmias. Detection is accomplished through the use of a multitude of spatially oriented electrodes situated on a pacing lead to provide a vector representation of the direction of propagation of depolarization wavefronts.

Others, such as the inventors of U.S. Pat. No. 4,712,554, have proposed distinguishing between sinus and non-sinus atrial depolarizations by determining the sequence of atrial activation through the use of bipolar or quadra-polar electrodes placed high in the right atrium. U.S. Pat. No. 4,577,634 employs quadra-polar atrial and ventricular electrodes for distinguishing retrograde P-wave conduction from normal sinus propagation to avoid pacemaker mediated tachycardia. In a further U.S. Pat. No. 4,790,317, it is proposed to recognize ventricular tachycardia and ventricular fibrillation by comparison of pulse sequences which are obtained when sensing from at least one position on each ventricular epicardial surface. A change in the sequence of activations and in the timing of signals sensed at the two sensor positions is detected and used to indicate either ventricular tachycardia or ventricular fibrillation.

It has also been proposed in the article entitled "Measurement of Difference in Timing and Sequence Between Two Ventricular Electrodes as a Means of Tachycardia Differentiation", by Mercando et al, appearing in PACE, Vol. 9, pp. 1069–1078, November–December, 1986, Part II, that the use of two ventricular sensing electrodes to determine electrical activation sequence in the expectation that the sequence could provide a method for differentiation of normal from abnormal rhythms by implantable anti-tachycardia devices. Simultaneous recordings from two ventricular sites were obtained during implantation of several devices or programmed electrical stimulation studies. Recordings were made of normal sinus rhythm, ventricular tachycardia, and during premature ventricular contractions. The time intervals between the intrinsic deflections of the two electrograms derived from the ventricular electrodes were measured in a number of the patients and the mean and range values were derived. The authors concluded that the measured mean values of the time intervals over a series of beats could be employed in individual patients to differentiate between normal and abnormal complexes. However, while the authors concluded that it would be feasible to detect differences in sequence timing using two ventricular electrodes in order to distinguish normal sinus beats from ectopic beats, the disclosed range of mean time intervals shows considerable overlap.

Yet another proposal for distinguishing between various types of tachyarrhythmia and ventricular fibrillation is disclosed in U.S. Pat. No. 4,799,493 issued to DuFault. In the device disclosed in this patent, the Widrow-Hoff algorithm is utilized for estimation of a transfer function as a means of discriminating between tachyarrhythmias. The transfer function, once determined generates a replica (estimate) of the signal from a first electrode pair, based on the signal from a second electrode pair. The signal from the first electrode pair can be subtracted from the derived replica (estimate)

signal to produce a null signal, in the presence of stable rhythm. Filters specifically tuned to produce null signals in the presence of sinus tachycardia or ventricular tachycardia are disclosed, as well as adaptive filters which automatically converge in the presence of stable rhythm. The automatically adapting filters are disclosed as capable of distinguishing between ventricular fibrillation and tachycardias, in that the LMS algorithms will not allow convergence in the presence of fibrillation. This technique is also described in the article "Dual Lead Fibrillation Detection for Implantable Defibrillators Via LMS Algorithm" by DuFault et al., published in *Computers and Cardiology* 1986, IEEE Computer Society Press, pp. 163-166.

In commonly assigned U.S. Pat. No. 5,193,535 to Bardy et al., a method and apparatus for reliable discrimination of ventricular fibrillation from high rate monomorphic ventricular tachycardias is set forth wherein the cumulative variability of the time intervals separating the occurrence of first and second "fiducial points" of a single QRS complex over a series of beats is used to distinguish fibrillation from high rate ventricular tachycardia. The ventricular tachycardia/ventricular fibrillation discriminator of the '535 patent preferably employs a pair of widely spaced or "far field" electrodes and a further pair of far field electrodes or two narrowly spaced or "near field" electrodes. Each electrode pair is coupled to detection circuitry for identifying the points in time at which the sensed electrical signals resulting from the passage of a QRS depolarization wavefront meet certain predetermined criteria, referred to as the first and second "fiducial points".

Identification of the time of occurrence of a first defined fiducial point in the sensed signal from one of the electrode pairs may be used to define a time window during which the device attempts to identify a second fiducial point in the sensed signal from the other electrode pair. The time interval separating the two fiducial points associated with a single detected depolarization wavefront is measured and stored. The cumulative variability of the value of the time interval over a series of detected depolarization wavefronts in conjunction with detection of a high ventricular rate is used to distinguish ventricular fibrillation from high rate tachycardia.

In addition, various detection and discrimination schemes have been proposed to distinguish or classify arrhythmias based on morphology. For example, U.S. Pat. No. 5,086,772 to Larnard et al. discloses an implantable arrhythmia control system for recognizing and classifying bradycardia, normal rhythm, tachycardia, electrical interference and ventricular fibrillation and delivering an appropriate therapy, if necessary. In one of the approaches taken to classify a waveform, the variability of R-wave interval (rate), R-wave width, and polarity is monitored (optionally with P-wave detection, P-R interval and rate in a dual chamber system) along with the morphology of the a windowed portion of the R-wave. The R-wave is sensed by an R-wave sense amplifier preferably coupled to a pair of bipolar ventricular electrodes and an event detect is made on the sensed peak of the R-wave. The R-wave sense amplifier output is continuously digitized, and a window running forward and backward in time is applied to the digitized data at event detect. The windowed data is used in morphology analysis with respect to a stored normal sinus rhythm (NSR) template created in initialization of the device at start-up, presumably at implant, and periodically updated. The morphology characteristics are stated to be R-wave width and polarity at col. 5, lines 50-63, and are calculated in column 8, lines 8-25. These characteristics are determined for each detected R-wave, and the values are compared to thresholds related to the most recently stored NSR R-wave to distinguish between intact normal conduction beats and ectopic beats. The event classification of abnormal polarity and/or width increments an output event value to a "rhythm sum" in the rhythm classification algorithm.

SUMMARY OF THE INVENTION

The tachycardia/fibrillation discriminator of the present invention is intended to be used in conjunction with an implantable pacemaker/cardioverter/defibrillator which provides differing therapies for detected ventricular tachycardias and detected ventricular fibrillation. For example, in response to detection of a tachycardia, the device may provide burst pacing, overdrive pacing or some other anti-tachycardia pacing regimen. Alternatively, it may provide a low to high energy cardioversion pulse. Typically, in response to detection of fibrillation, the device will provide a defibrillation pulse at an amplitude significantly higher than a cardioversion pulse.

In accordance with the invention, apparatus for and a method of operating such apparatus is provided wherein a fiducial point of each successive QRS complex is detected prompting the storage of sampled and digitized waveform data within a timing window bridging the point in time of fiducial point detection. Stored sets of such sampled waveform data are compared data point to data point resulting in a sampled morphology index value for each compared set. The magnitude of the sampled morphology index value or a series such index values are analyzed to determine the presence of a single or a progression of beat-to-beat waveform changes indicative of a polymorphic single transition or progression of QRS complexes from monomorphic to polymorphic waveforms indicative of an arrhythmia that should be treated with aggressive cardioversion/defibrillation therapies.

The apparatus and method of operating preferably employs closely spaced and widely spaced pairs of electrodes for sensing each QRS complex of the patient's electrocardiogram (EGM). The closely spaced electrode pair is coupled to sense detect circuitry for identifying a predetermined fiducial point in the electrical signal associated with a ventricular depolarization and to counting and comparison circuitry for developing rate and onset data. The widely spaced pair of electrodes is coupled to sense and digitizing circuitry for developing the sampled waveform amplitude data from which the morphology index values are derived.

Preferably, the morphology index values are only derived when other detection criteria, e.g. rate and/or onset are satisfied. It is believed that the invention is optimally embodied in a device which is capable of differentiating between low rate tachycardia, high rate tachycardia and fibrillation, and which provides three increasingly aggressive therapy sets for these three classes of arrhythmias. Detection of low rate tachycardias may be accomplished using any of the numerous detection methodologies known to the art, as applied to detected heart rates exceeding a lower tachycardia detection rate. The tachycardia/fibrillation discriminator of the present invention in such a device will typically be dependant on detection of a heart rate substantially in excess of the lower tachycardia detection rate.

In such devices, the discriminator will serve primarily to distinguish between high rate tachycardia and fibrillation.

The method and apparatus of the present invention may be conveniently realized by providing a first pair of endocardial, myocardial or epicardial electrodes spaced apart from one another in or on the ventricles of the heart and a second pair of electrodes which may, for example, include one of the electrodes of the first pair and a large surface defibrillation electrode or a remote, indifferent electrode such as the metal housing of the implantable cardioverter/defibrillator. Alternatively, the second electrode pair might be two large surface defibrillation electrodes. Sense amplifiers are provided for each electrode pair.

The ventricular electrode pair and its associated sense amplifier detects the near field, bipolar electrogram, and the fiducial point may be determined at the output of the near field sense amplifier in a manner corresponding to traditional R-wave detection criteria known to the art. For example, the peak amplitude output signal from the near field sense amplifier may be employed to define the time of occurrence of the fiducial point and also may be used for measuring the duration of the intervals separating ventricular depolarizations (R-R intervals) to determine whether the heart rate is sufficiently rapid to activate or to continue the tachycardia/fibrillation discrimination function at the point of determining whether the instantaneous rhythm is polymorphic or not.

The other, widely spaced, electrode pair is connected to a far field sense amplifier and A/D conversion circuit for sampling and digitizing the far field EGM. The far field EGM is cumulative of the individual myocardial cell depolarizations of a greater mass of cells and manifests a wider R-wave than the near field EGM signal. Consequently, a window may be defined for the storage and comparison of the far field EGM wave shape data sets at the point in time when the fiducial point is detected from the near field EGM or R-wave peak.

The measurement of cumulative morphology index variability may be accomplished by FIFO summation of a running series of morphology index values. Alternatively, each index value that exceeds a threshold index value may increment a counter on a FIFO basis so that the count provides an indication of the degree to which the rhythm is polymorphic. Other measures of cumulative variability may also be employed.

The present invention advantageously may be employed to augment or confirm or as a substitute for certain adjunct detection criteria employed in the above referenced '535 or '772 patents. The beat-to-beat morphology index value provides a high degree of sensitivity to progression in chaotic EGM activity accompanying the transition from benign or sinus tachycardia to malignant tachycardia and fibrillation. Through the use of a further bipolar atrial electrode pair and near-field P-wave sense amplifier for providing a P-wave fiducial point, it may be possible to distinguish atrial arrhythmias and retrograde conduction from NSR.

The use of the near field EGM derived fiducial point avoids difficulties that arise in the identification of the appropriate fiducial point from the wider, and less "peaked", that is, lower slope or rise time, far field EGM. The recognition that it is not important to precisely determine a fiducial point of the wave shape data to be compared as satisfying a strict identity criteria in successive wave shape data sets is an important advantage of the invention as realized in its various embodiments.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

The figures are not necessarily to scale.

DETAILED DESCRIPTION OF THE PREFERRED EMBODIMENTS

Certain of the figures and the description set forth hereafter corresponds to figures in the above referenced '535 patent incorporated herein by reference in its entirety. The same pacemaker/cardioverter/defibrillator systems, including the same electrodes, sense amplifiers and fiducial point detectors, may be employed in the practice of the present invention, which may be incorporated into or substituted for the variability in fiducial point time intervals criteria set forth therein.

Figure 1:
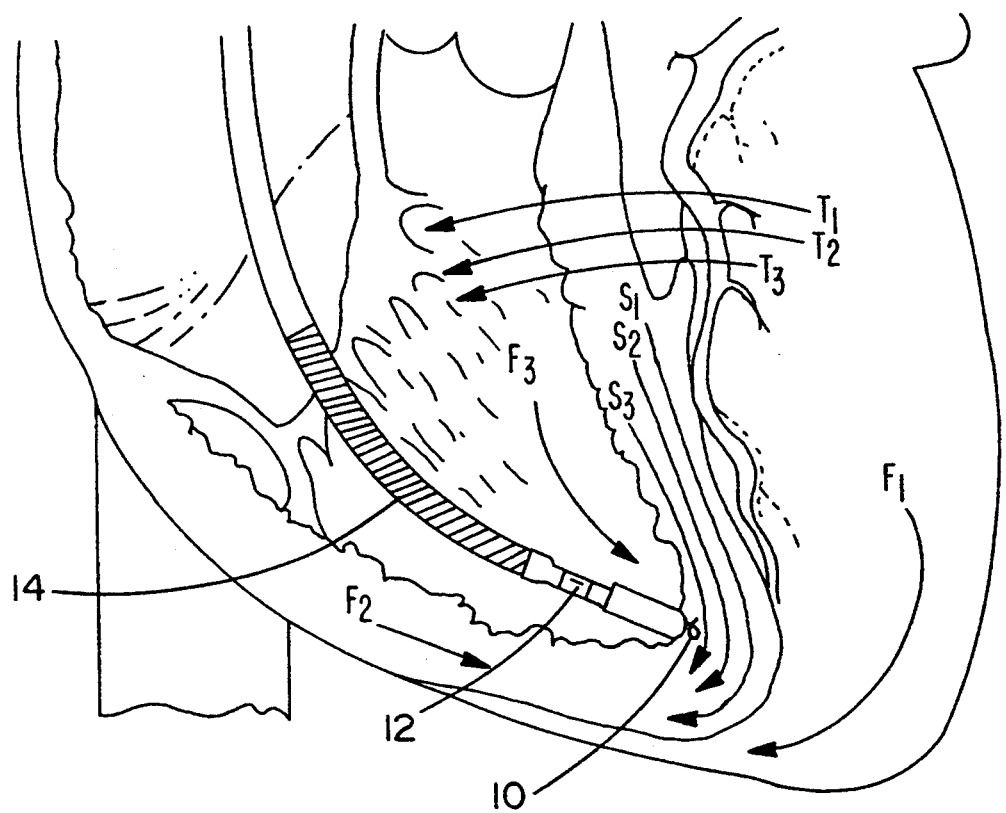
FIG. 1 is a representation of the heart, and an implanted electrode lead, illustrating the theory underlying the present invention.

FIG. 1 is a cutaway view of the heart, illustrating a ventricular defibrillation lead carrying a bipolar electrode pair located at the right ventricular apex. The bipolar electrode pair includes a tip electrode 10, which takes the form of a helical electrode screwed into the right ventricular myocardium and a ring electrode 12. The lead also includes an elongated coiled defibrillation electrode 14. The illustrated lead corresponds generally to one of the lead sets described in the above-referenced '535 patent, but other defibrillation leads may also be employed.

In conjunction with FIG. 1, it should be understood that the electrode pair used to sense the near field EGM and to derive the R-wave sense detect fiducial point discussed above may include ring electrode 12 and tip electrode 10. The other electrode pair used to sense the far field EGM may include ring electrode 12 and a second electrode, typically one of the defibrillation electrodes included in the lead system implanted with the pacemaker/cardioverter/defibrillator, e.g. electrode 14 in the example depicted in FIG. 1.

The general path of propagation of three successive depolarization wavefronts associated with a sinus rhythm is illustrated by the arrows labeled "S1, S2, S3". The wavefronts proceed down the septum of the heart, and then expand outward and upward around the right and left ventricles. This pathway of propagation also is present in the case of a supraventricular tachycardia such as a nodal tachycardia or a sinus tachycardia, and is consistent from beat to beat. As a result, the near and far field EGMs are typically relatively uniform in wave shape amplitude from beat to beat.

An example of the general path of propagation of three successive depolarization wavefronts associated with a monomorphic ventricular tachycardia is illustrated by the arrows labeled "T1, T2, T3". In the case of monomorphic ventricular tachycardia, the direction of propagation, with respect to any particular electrode pair may be the same or different from that of normal sinus rhythm (NSR). However, the direction of propagation will be approximately the same from beat to beat for a run of beats. Again, the near and far field EGMs will appear to be relatively uniform, exhibiting a monomorphic time and amplitude wave shape from beat to beat.

Also illustrated are examples of the directions of propagation of three successive depolarization wavefronts associated with ventricular fibrillation, illustrated by the arrows labeled "F1, F2, F3". The hallmark of ventricular fibrillation is the chaotic variation in the spread of the activation wavefront from depolarization to depolarization as opposed to constancy of wavefront propagation from depolarization to depolarization as seen in NSR, supra-ventricular tachycardia (SVT) or monomorphic ventricular tachycardia (VT). As illustrated, the direction of wavefront propagation past electrode pairs 10, 12 and 10, 14 varies substantially from one wavefront to the next.

Because of the stable electrode positions, the variability in the direction of wavefront propagation causes the wave shape of the EGM to vary with direction. In NSR or in VT or SVT, beat to beat variability in wave shape only changes with heart rate, as the QRST complex narrows with rate increase.

It is this beat to beat variability in the direction of wavefront propagation and the manifested changes in the wave shape of the far field EGM, normalized to a fiducial point, during fibrillation that allows the discriminator of the present invention to assist in distinguishing ventricular fibrillation from ventricular tachycardia, whether the tachycardia takes the form of a VT, SVT, or a sinus tachycardia. Moreover, the principles of the present invention may be employed in the atrium to distinguish atrial arrhythmias from sinus rhythms.

Figure 2:
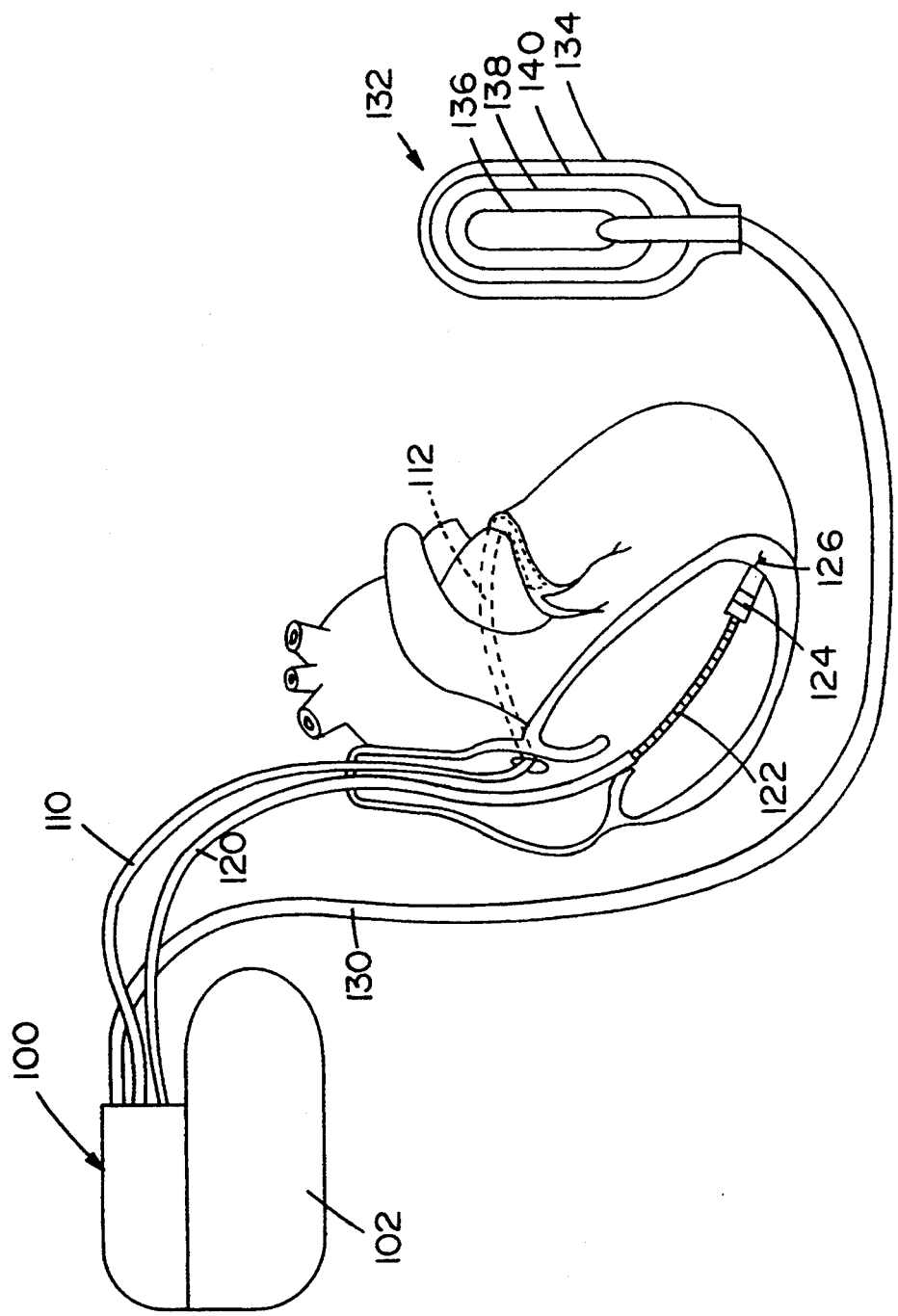
FIG. 2 illustrates a transvenous/subcutaneous electrode system appropriate for use with a pacemaker/cardioverter/defibrillator embodying the present invention.

FIG. 2 illustrates an implantable pacemaker/cardioverter/defibrillator 100 and its associated lead system, as implanted in and adjacent to the heart and corresponding to the system disclosed in FIG. 2 of the '535 patent. As illustrated, the lead system comprises a coronary sinus lead 110, a right ventricular lead 120, and a subcutaneous lead 130. The coronary sinus lead is provided with an elongated electrode located in the coronary sinus and great vein region at 112, extending around the heart until approximately the point at which the great vein turns downward toward the apex of the heart. The right ventricular lead 120 corresponds to the lead illustrated in FIG. 1 and includes an elongated defibrillation electrode 122, a ring electrode 124, and helical electrode 126, which is screwed into the tissue of the right ventricle at the right ventricular apex. A subcutaneous lead 130 is also illustrated, implanted subcutaneously in the left chest. Lead 130 includes a large surface electrode pad 132, carrying elongated electrode coils 136, 138 and 140.

In conjunction with this embodiment of the present invention, the lead systems illustrated in FIG. 2 provide a bipolar, near field electrode pair and numerous far field electrode pairs which may be employed to practice the invention. For example, the near field electrode pair comprises ring electrode 124 and tip electrode 126, and the far field electrode pair comprises ring electrode 124 and subcutaneous defibrillation electrode 132. Alternatively, the far field pair of electrodes could comprise defibrillation electrode 112 in conjunction with the subcutaneous electrode 132, or in conjunction with defibrillation electrode 122. In addition, the pulse generator case 102 may be employed as one of the far field electrodes.

Other far field electrode pairs may instead comprise small surface area electrodes (not illustrated) provided on the lead bodies of the coronary sinus lead 110 and/or the ventricular lead 120. For example, an additional electrode or electrode pair could be mourned to the coronary sinus lead or to the ventricular lead such that the electrode or electrode pair would be located high in the ventricle or in the superior vena cava when implanted.

Figure 3:
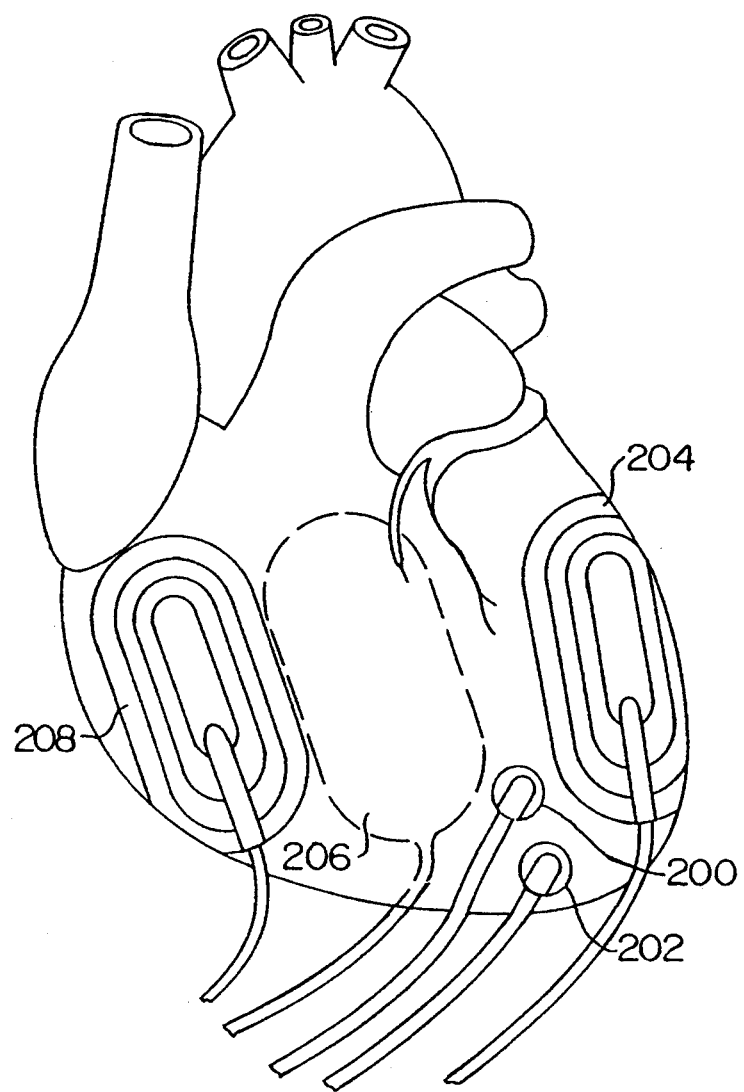
FIG. 3 illustrates a myocardial/epicardial electrode system appropriate for use with a pacemaker/cardioverter/defibrillator embodying the present invention.

FIG. 3 (corresponding to FIG. 3 of the '535 patent) illustrates an epicardial and myocardial electrode system for use in conjunction with an implantable pacemaker/cardioverter/defibrillator in accordance with the invention. In this case, two unipolar myocardial electrodes 200 and 202 are located on the left ventricle of the heart. Also illustrated are three large surface electrodes 204, 206 and 208, spaced around the ventricles of the heart.

In the context of the present invention, electrodes 200 and 202 constitute the near field electrode pair, and the far field electrode pair may include either of electrodes 200 and 202 in conjunction with one of the large surface defibrillation electrodes 204, 206, 208 or may comprise two of the defibrillation electrodes. Alternatively, the near field electrode pair might comprise electrode 200 in conjunction with the closest one of the large surface electrodes 204, 206, 208 (electrode 204 as shown), and the other small surface area electrode 202 might be eliminated. As a practical matter, in the systems as illustrated in FIGS. 1-3, a pair of small surface area electrodes corresponding generally to electrodes 10 and 12 in FIG. 1, electrodes 124 and 126 in FIG. 2 or electrodes 200 and 202 in FIG. 3 will generally be used for delivery of cardiac pacing pulses and for sensing the occurrence of R-waves in order to reset the timing of the cardiac pacing function and for most purposes associated with tachyarrhythmia recognition, including interval (rate), onset (change in rate) and regularity. The invention may conveniently be practiced by employing any of the depicted near field electrode pairs in conjunction with an R-wave detector of a known type to provide a signal indicative of the occurrence of a fiducial point as discussed above which is that point in time that a sense detect occurs. In such sense amplifiers, the characteristics of which are well known in the art, sense detect occurs at that point when the varying amplitude of the QRS wave shape of the R-wave containing EGM exceeds a preset threshold voltage or reaches a maximum (peak) value. In microprocessor based timing and control systems, sense detect may set a flag and prompt the detection of the R—R interval and reset the bradycardia pacing timing circuit.

In the case illustrated in FIG. 1, the first electrode pair, including electrodes 10 and 12, will sense a different electrical signal from the second electrode pair, including electrode 12 and a subcutaneous electrode or defibrillation electrode. With varying direction of waveform propagation, the wave shapes at any two electrode pairs will vary from beat to beat.

Figure 4:
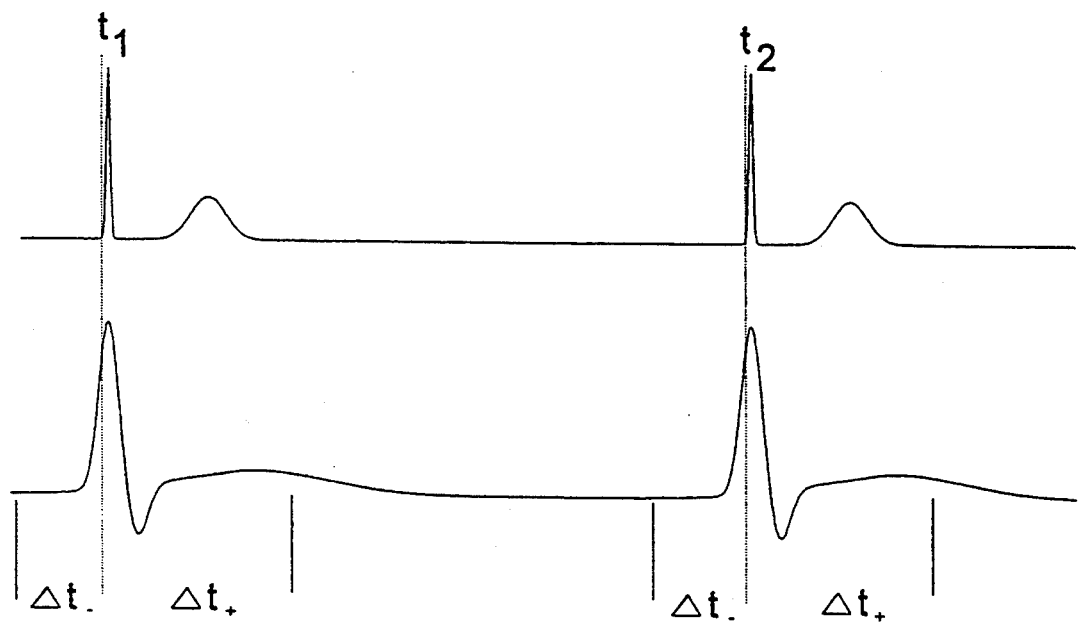
FIG. 4 is an illustration of the identification of the first and second fiducial points in a sequence of two near field R-waves, and the setting of the timing windows with respect to the corresponding far field, sampled and digitized EGM data sets.

FIG. 4 is a set of idealized EGM tracings illustrating the detection of the fiducial point associated with a near field R-wave and the setting of a timing window within which the sampled and digitized amplitude of the wave shape of the far field R-wave is stored as a wave shape data set for first and second successive ventricular depolarizations or beats. The analog signal amplitude of the far field EGM is continuously sampled at a certain sampling frequency, digitized, and temporarily stored on a FIFO basis. The timing window constitutes a predetermined number of sampled data points preceding and following the fiducial point constituting a fixed number data set and corresponding to a cardiac cycle. When the fiducial point is detected, the contemporaneously sampled and temporarily stored data set is transferred to memory as a reference wave shaped data set against which a subsequent data set is compared to derive a set of difference values which may be summed to derive a morphology index value.

As illustrated, the top EGM tracing is taken between an electrode pair located in the right ventricle, comprising a tip and ring electrode generally corresponding to electrodes 124 and 126 illustrated in FIG. 2. The lower tracing is taken between the proximal one of the bipolar pair in the right ventricle, corresponding generally to electrode 124, and a remote, subcutaneous electrode, for example.

The fiducial point identified by the processing circuitry coupled to the first electrode pair, in the upper tracing, corresponds to the output of an R-wave detection circuit employing a bandpass filter followed by a detector having an automatically adjusting threshold level. The occurrence of the fiducial points, illustrated by the times $t_1$ and $t_2$, occurs when the band pass filtered signals from the near field electrode pair exceeds the detection threshold. As specifically illustrated in the upper tracing of FIG. 4, the R-wave detect provided by the near field sense amplifier occurs on the rising slope of the wave shape. The specific sense amplifier employed is incorporated in the MEDTRONIC Model 7218 pacemaker/cardioverter/defibrillator. The operation of the R-wave detection circuitry may correspond to that disclosed in U.S. Pat. No. 5,117,824, to Keimel, et al., incorporated herein by reference in its entirety. However, alternative R-wave detection circuitry such as that illustrated in U.S. Pat. Nos. 4,819,643 to Menken and 4,880,004 to Baker et al., both incorporated herein by reference in their entireties, may also usefully be employed to practice the present invention. A peak detect sense amplifier could also be used as suggested above. In any case, the output of the near field sense amplifier is itself In the lower tracing, the timing windows $\Delta t_-$, $\Delta t_+$ preceding and following each fiducial point at times $t_1$ and $t_2$ are illustrated in reference to the far field EGM encompassed thereby. The wave shape data sets are derived from the sampled and digitized wave shape data encompassed within the timing windows. For example, the sampling rate may be 256 to 512 samples per second.

In use of the actual sense detect of the amplifier and near field electrode pair, some beat-to-beat "jitter" in the fiducial points may manifest itself. This jitter, if it occurs, is within an approximately ±10–20 ms. window centered on the sense detect output fiducial points at times $t_1$ and $t_2$, and corresponds to about 5–20 sample points of the far field EGM, depending on the sample rate and window size. It is possible to fine tune the identification of the successive fiducial points from times $t_1$ and $t_2$ by a cross-correlation of the far field sample values within the 20–40 ms. windows to precisely identify the alignment of the sample point values of the far field EGM showing the greatest degree of correlation, i.e. the lowest sum of the sample point difference values. If this is done, it may result in a shift of one or more sample points in the precise identification of the second fiducial point at time $t_2'$ with respect to the first fiducial point at time $t_1$. As a result, certain of the sample point data values of each data set at the extremes of the overall sample timing windows $\Delta t_-$, $\Delta t_+$ preceding and following each fiducial point may lack a counterpart in the other data set and be disregarded. To accommodate this possibility, the sample timing windows $\Delta t_-$, $\Delta t_+$, may be expanded by the width of the cross correlation windows selected and the number of sampled data values compared after alignment may be fixed to a lesser number than initially digitized and stored within the expanded windows. In this fashion, it can be assured that every morphology comparison involves the same number of sampled data values for every successive data set.

Figure 5:
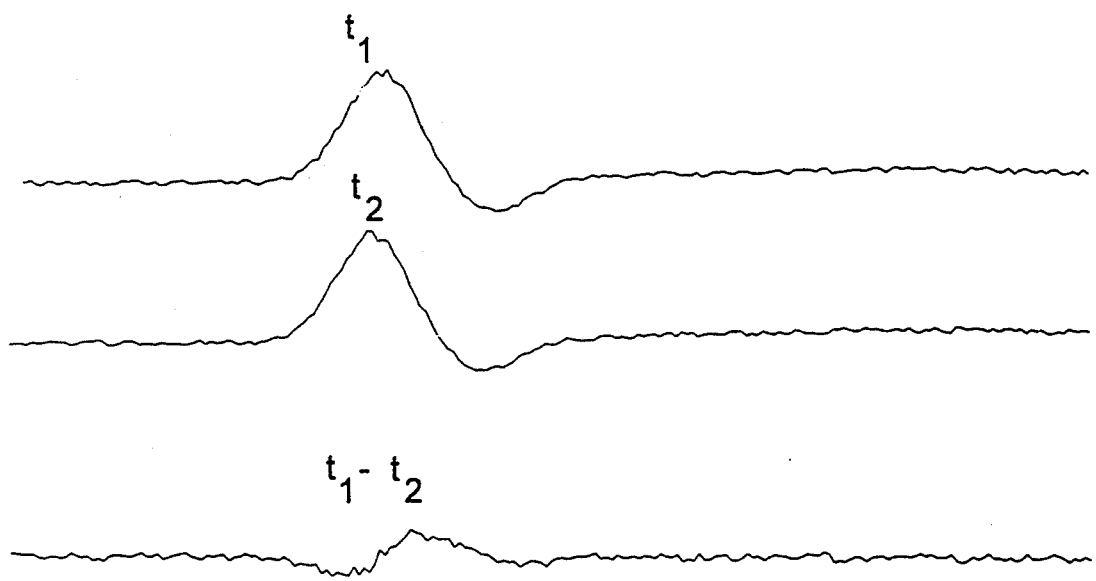
FIG. 5 is an illustration of the alignment of the first and second fiducial points and the derivation of the sample point to point amplitude difference values that are representative of the morphology of the two aligned far field R-wave data sets of FIG. 4.

The successive fiducial points defined by the processing circuitry associated with the near field electrode pair and the fine tune alignment described above provides the point of alignment of the wave shape data sets for sample point to point comparison to derive a morphology data set. FIG. 5 is an idealized illustration of the alignment of the first and second far field EGMs of FIG. 4 with respect to the fiducial points at times $t_1$ and $t_2$. By subtraction of the values of each corresponding digitized data point, the difference data values for each point are depicted in the third tracing. The difference data values may be summed to derive a digital morphology index value which is typically small when monomorphic wave shapes are compared and increases as successive cardiac cycles become polymorphic.

The first and second data sets illustrated in FIG. 5 may for the sake of simplicity and immediacy be successive pairs of data sets analyzed contemporaneously with the satisfaction of adjunct criteria. However, they need not be successive wave shape data sets, but may be a current data set compared to a reference data set or a preceding data set in a series of wave shape data sets.

As defined in the present application, a threshold index value is established for a patient which may constitute an average of a series of morphology index values for a series of NSR beats at the same or differing heart rates multiplied by a safety factor exceeding 1.0. A set of threshold values may be derived from separate series of NSR beats for differing heart rate ranges, wherein the threshold value may be selected as a function of current heart rate. In addition, the threshold values may be periodically updated either by a programmed-in update command or automatically.

However, a simple, single threshold index value based on NSR is preferred, since it is recognized that the general detection and treatment philosophy would be biased toward the detection of a life threatening arrhythmia given the satisfaction of the adjunct criteria. For this reason, a single, robust (i.e., not dependent on rate ranges or duration of the high rate or other adjunct criteria) threshold index value based on the difference between successive NSR beat morphology index values is sufficient. For example, a simple, robust threshold index value that constitutes 200% of the average of a short series of NSR morphology index values will suffice to provide the confirmation of the arrhythmia.

Figure 6:
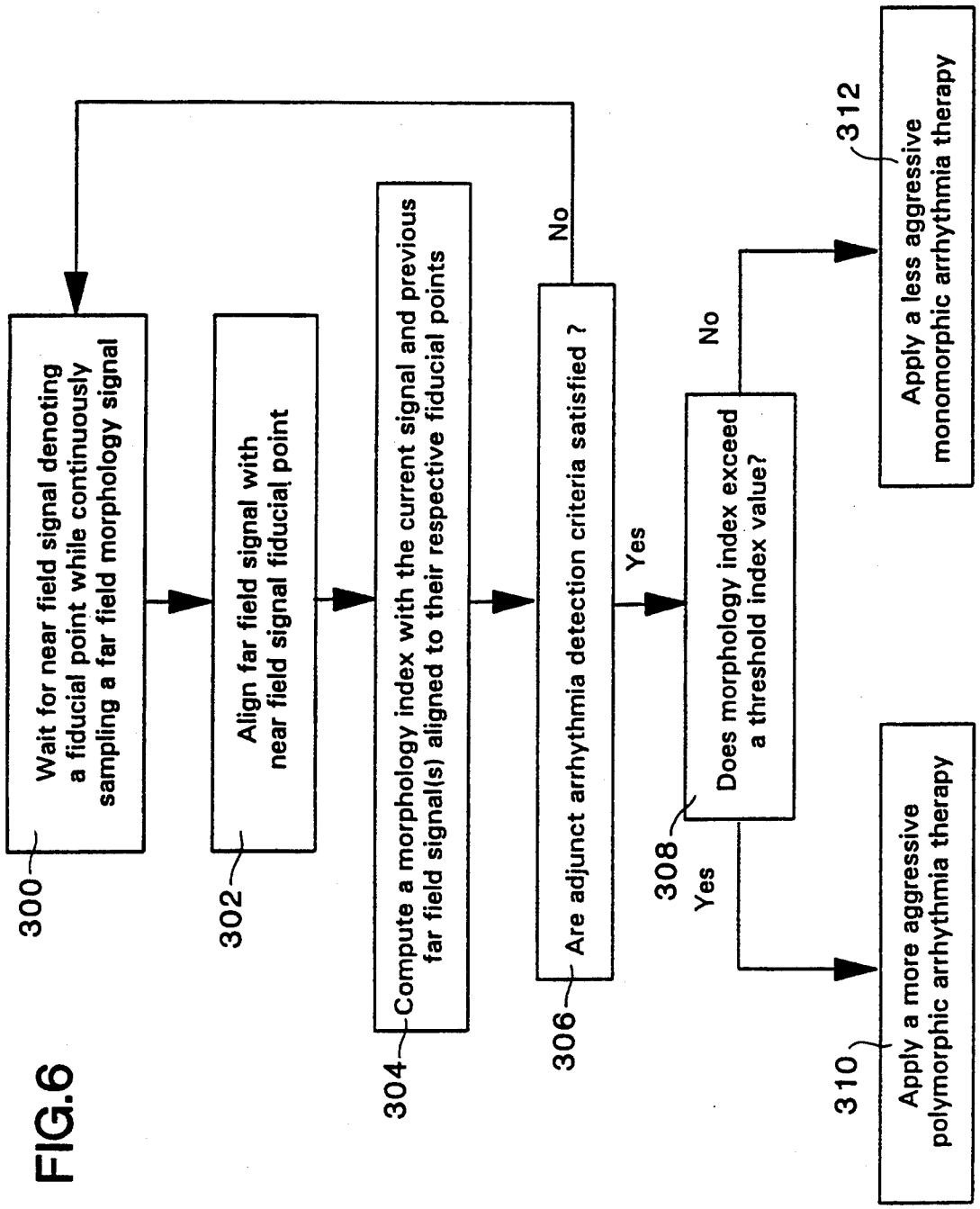
FIG. 6 is a general flow chart of a preferred method of deriving a morphology index from successive depolarizations of either chamber of the heart, classifying the rhythm and employing the classification in directing the appropriate arrhythmia therapy to be delivered by the pacemaker/cardioverter/defibrillator.
Figure 7:
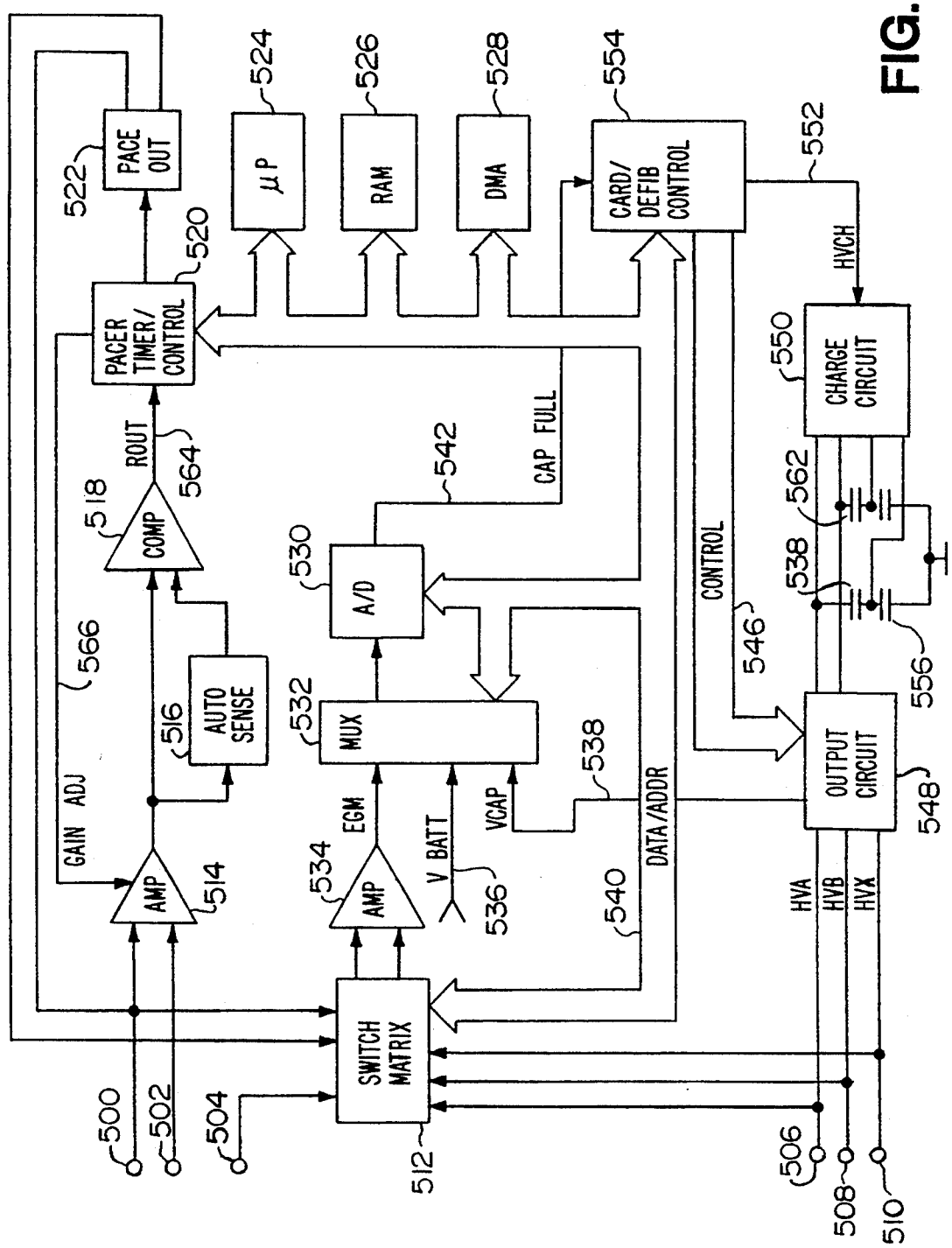
FIG. 7 is a schematic block diagram illustrating the structure of one embodiment of an implantable pacemaker/cardioverter/defibrillator in which the present invention may be embodied.

FIG. 6 illustrates one method of the operation of the tachycardia/fibrillation discriminator operative on the data sets illustrated in FIGS. 4 and 5 which may be readily incorporated into the pacemaker/cardioverter/-defibrillator depicted in FIG. 7.

FIG. 7 is a functional schematic diagram from the '535 patent of an implantable pacemaker/cardioverter/-defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/cardioverter/defibrillators presently being implanted for clinical evaluation in the United States. The invention is also believed practicable in conjunction with implantable pacemaker/cardioverter/defibrillators as disclosed in prior U.S. Pat. Nos. 4,548,209, to Wielders et al., 4,693,253, to Adams et al., 4,830,006, to Haluska et al., and 4,949,730, to Pless et al., all of which are incorporated herein by reference in their entireties.

The device is illustrated as being provided with six electrodes, 500, 502, 504, 506, 508 and 510. Electrodes 500 and 502 may be a pair of closely spaced electrodes located in the ventricle, for example, corresponding to electrodes 124 and 126 in FIG. 2. Electrode 504 may correspond to a remote, indifferent electrode located on the housing of the implantable pacemaker/cardioverter/defibrillator. Electrodes 506, 508 and 510 may correspond to the large surface area defibrillation electrodes located on the ventricular, coronary sinus and subcutaneous leads illustrated in FIG. 2 or to the epicardial electrodes 204, 206 and 208 of FIG. 3.

Electrodes 500 and 502 are shown as hard-wired to the near field, R-wave detector circuit, comprising bandpass filtered amplifier 514, auto threshold circuit 516 (for providing an adjustable sensing threshold as a function of the measured R-wave amplitude) and comparator 518. A signal is generated on ROUT line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al, published in Biomedical Science Instrumentation, Vol. 4, pp 67–72, 1978, incorporated herein by reference in its entirety.

It is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1–3 seconds following adjustment of the sensing threshold equal to 70–80% of the amplitude of a detected spontaneous R-wave.

In any case, each successive R-wave sense event signal on the ROUT line (in this example) constitutes the fiducial point signal $t_1$ employed in the present invention to set the timing windows and to align the successive wave shape data sets for comparison and subtraction of each data point and to derive the cumulative morphology index as described above. In this context, the sense event signal is routed through the pacer/timer control circuit block 520 on data bus 540 to the microprocessor 524, where it operates as an interrupt commencing a number of operations as described further below. It will be understood that the alternative sense amplifiers described above may be substituted for bandpass filtered amplifier 514, auto threshold circuit 516 and comparator 518 to develop the fiducial point signal $t_1$ as a function of the rise time of the near field R-wave as depicted in FIG. 4.

Switch matrix 512 is used to select which of the available electrodes make up the second electrode pair for use in conjunction with the present invention. The second electrode pair may comprise electrodes 502 and 500 or electrode 500 in conjunction with one of the electrodes 504, 506, 508 or 510, or may comprise other combinations of the illustrated electrodes, including combinations of the large surface defibrillation electrodes 506, 508, 510. Selection of which two electrodes are employed as the far field electrode pair in conjunction with the tachycardia/fibrillation discrimination function is controlled by the microprocessor 524 via data/address bus 540. Far field EGM signals from the selected electrodes are passed through bandpass amplifier 534 and into multiplexer 532, where they are converted to multi-bit digital signals by A/D converter 530, for storage in random access memory 526 under control of direct memory address circuit 528. Storage of a series of EGM complexes over several seconds on a FIFO basis is contemplated.

In this regard, the operating system of the pacemaker/cardioverter/defibrillator may include the capability of permanently storing EGM data of the most recent or several recent tachyarrhythmic episodes on a FIFO basis. Permanent storage is triggered by confirmation and classification of the arrhythmia and includes the digitized far field EGM for a period preceding confirmation, through delivery of the programmed therapies and for a subsequent time period. That operating system may be readily modified in accordance with the teachings of the present invention to effect the morphology comparison and classification method set forth in FIG. 6 by employing the near field R-wave (or P-wave, if a dual chamber system is implemented) sense event as the fiducial point and the sampled and digitized far field EGM wave shape data sets continuously and temporarily stored in random access memory 526. Thus, in such a system already configured to store episodes, the morphology index values of successive sets oft wave shape data may be derived continuously. In systems not having data storage of the type described, it may be desirable, to save operating energy, to only commence A/D conversion by A/D converter 530 and morphology analysis after one or more adjunct tachyarrhythmia criteria are satisfied.

As discussed above, switch matrix 512 selects which of the various electrodes are coupled to band pass amplifier 534. Amplifier 534 may be a broad band pass amplifier, having a band pass extending for approximately 0.5 to 200 hertz. The filtered EGM signal from amplifier 534 is passed through multiplexer 532, and digitized in A/D converter circuitry 530. For purposes of the present invention, a sampling rate of 256 to 512 samples per second should be sufficient, although somewhat lower or substantially higher sampling rates may be used, depending on the amount of data storage capacity in RAM 526 and on the processing speed of microprocessor 524. The sampled and digitized data is stored in random access memory 526 under control of direct memory address circuitry 528. Preferably, a portion of random access memory 526 is configured as a looping or buffer memory which stores at least the preceding several seconds of the EGM signal on a FIFO basis.

The occurrence of an R-wave sense event or detect signal on ROUT line 564 is communicated to microprocessor 524 via data/address bus 540, and microprocessor 524 notes the time of its occurrence. Microprocessor 524 waits 100 milliseconds following the occurrence of each successive R-wave detect signal, and thereafter transfers the most recent 200 milliseconds of digitized EGM wave shape data stored in the looping or buffer memory portion of the random access memory circuit 526 to a secondary memory location, where the successive wave shape data sets are aligned by their respective fiducial points to one another.

For example, as illustrated in FIG. 4, the microprocessor 524 may, in response to an R-wave sense event signal on ROUT line 564, temporarily separately store the EGM wave shape data set over the window comprising interval $\Delta t_-$ extending from minus 100 milliseconds previous to the occurrence of the R-wave sense event signal, until $\Delta t_+$ or 200 milliseconds following the occurrence of the R-wave sense event signal, in order to perform the morphology analysis with a subsequently windowed and stored EGM wave shape data set. The data sets are aligned to the near field R-wave sense event fiducial points $t_1$, $t_2$, and the morphology index is computed by subtraction of the values of each aligned data point and the addition of the difference values by the microprocessor 524. The morphology index may then be compared to a threshold index value retrieved from RAM 526 to classify the most recent R-wave event as monomorphic or polymorphic. The classification may be stored, and, when adjunct tachyarrhythmia criteria are satisfied, the classification may be employed in the selection of the therapy as described above in reference to FIG. 6.

As described above, the fine tune alignment of the successive fiducial points $t_1$, $t_2$, may be accomplished by cross correlation of the sampled and digitized far field data values within the $\pm 10$-$20$ ms. windows on either side of the successive fiducial points $t_1$, $t_2$, seeking the alignment in the shifted data that results in the least difference sum. As described above, as the sampled data is shifted, certain of the sample point data values at the extremes of each of the $\pm 10$-$20$ ms. windows will not be aligned with a counterpart data value and that value may be ignored in the computation of the least difference sum. All computations of the fine tune alignment and the morphology of the aligned far field EGM data sets is accomplished within the microprocessor 524.

The morphology threshold index may be externally programmed into RAM 526 through a programming-/interrogation interface in a manner well known in the art. For example, the initially selected threshold index may be derived during a work up of the patient wherein arrhythmias may be induced and programmed in recognition criteria may be tested to confirm the ability of the criteria to recognize and arrhythmia and to properly classify it. The programmed-in recognition criteria may include the adjunct criteria described above as well as threshold indexes temporarily programmed into RAM 526 which are retrieved and employed by the operating system. Once an effective index threshold is arrived at, it may be transferred to permanent memory.

Each of the alternative or additional functions described above for derivation of the threshold index value from NSR events, the updating of the threshold index value, the detection of a progression from monomorphic to polymorphic wave shape, the storage of the number of successive polymorphic R-wave events or the proportion of such events among a series of N events may all be accomplished by suitable programming of the microprocessor 524 for manipulating the near field and far field EGM data to effect data storage and to trigger and deliver the appropriate therapy to the pacing or cardioversion/defibrillation electrodes.

The adjunct detection criteria include sustained high rate, onset and irregularity in the heart beat rate of the patient as described above. Microprocessor 524 measures the time intervals $\delta$ separating the R-wave sense events, and stores the measured intervals in random access memory 526. Microprocessor 524 also calculates the cumulative beat to beat variability of the values of $\delta$ over a preceding predetermined number of measured values of $\delta$, according to either of the method disclosed above, and determines whether the cumulative variability is indicative of fibrillation or ventricular tachycardia in a manner known in the art. After the desired number of values for $\delta$ are recorded, and in response to the detection of a heart rate of sufficient rapidity to indicate the occurrence of either ventricular tachycardia or fibrillation, the microprocessor calculates the cumulative variability in the values for $\delta$, according to either method described above. The calculated cumulative variability is compared to a predetermined threshold value to distinguish high rate sinus tachycardia from life threatening tachycardias and ventricular fibrillation.

Other variations on the adjunct arrhythmia detection criteria set fort in the above incorporated '535 patent may be employed in the practice of the present invention and are not repeated here. Such detection algorithms for recognizing tachycardias are also described in the above cited '380 patent, U.S. Pat. No. 4,880,005, issued to Pless et al and the '006 patent, incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in

*Computers in Cardiology*, Oct. 7–10, 1986, IEEE Computer Society Press, pages 167–170, also incorporated by reference in its entirety herein. However, other criteria may also be measured and employed in conjunction with the present invention. The cumulative effect of the detection criteria selected should enhance the discrimination of tachyarrhythmias. The present invention is readily incorporated into the pacemaker/cardioverter/defibrillator systems (with episode data storage) disclosed in '535 patent and may be selectable as a programmable option by the physician.

The remainder of the circuitry of FIG. 7 is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the tachycardia/defibrillation discrimination function.

Microprocessor 524 operates as an interrupt driven device, and responds to interrupts from pacer timing/control circuitry 520 corresponding to the occurrence of sensed R-waves (as described above) and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an anti-tachyarrhythmia pacing therapy regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in U.S. Pat. No. 5,188,105, to Keimel, and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585 to Zipes, in U.S. Patent No. 4,949,719 to Pless et al., cited above, and in U.S. Patent No. 4,375,817 to Engle et al., all incorporated herein by reference in their entireties may also be employed.

Similarly, known circuitry for controlling the timing and generation of antitachycardia pacing pulses as described in U.S. Pat. Nos. 4,577,633 to Berkovits et al., 4,880,005 to Pless et al., 4,726,380 to Vollmann et al., and 4,587,970 to Holley et al., all of which are incorporated herein by reference in their entireties may also be used.

Selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in commonly assigned, co-pending patent application Ser. No. 07/612,758, filed by Keimel, for an Apparatus for Delivering Single and Multiple Cardioversion and Defibrillation Pulses, filed Nov. 14, 1990, incorporated herein by reference in its entirety.

However, output control circuitry as disclosed in U.S. Pat. No. 4,953,551 to Mehra et al. or U.S. Pat. No. 4,800,883 to Winstrom, both incorporated herein by reference in their entireties, may also be used in the context of the present invention. Alternatively single monophasic pulse regimens employing only a single electrode pair according to any of the above cited references which disclose implantable cardioverters or defibrillators may also be used.

Referring again to FIG. 6, it is a simplified flow chart summarizing the general operation of the tachycardia/fibrillation discrimination functions that may be performed in the device illustrated in FIG. 7. FIG. 6 is intended to functionally represent that portion of the software employed by microprocessor 524 (FIG. 7) which implements the tachycardia/fibrillation discrimination function. This portion of the software is executed in response to an interrupt indicating the sensing of a ventricular depolarization of R-wave on ROUT line 564 at block 300. The time of detection $t_1$ of the sensed ventricular depolarization, as indicated by means of a real time clock within microprocessor 524, is also stored at block 300 and serves as the fiducial point associated with the detected depolarization.

At block or step 302, the microprocessor effectively creates the above described and depicted windows, aligned to the near field R-wave fiducial points, that defines the bounds of the sampled and digitized far field EGM wave shape data and transfers that data set to the secondary memory in RAM 526 for each successive R-wave sense event.

At block 304, the morphology index is computed by sample point to sample point comparison of the current and immediately preceding (or other reference data set as suggested above), digitized, far field data sets. The morphology index is then compared to the threshold index in block or step 308, in the manner described above, if the adjunct arrhythmia detection criteria are satisfied in block or step 306. If the morphology index of any two compared far field wave shape data sets exceeds the threshold index, then the rhythm is classified as "polymorphic" and a more aggressive therapy is prescribed in block or step 310. If the threshold index is not exceeded, then the rhythm is classified as "monomorphic" in block or step 312, and a less aggressive therapy is prescribed.

As summarized in FIG. 6, the above steps are conducted continuously and at least the most recent or a series of the rhythm classifications are stored in memory for a period of time or number of classifications. Moreover, the actual morphology index of a series of wave shape data sets may be stored on a FIFO basis so that a progressive increase in morphology index may be committed to permanent memory when the morphology index actually first exceeds the threshold index and, optionally, adjunct arrhythmia detection criteria are satisfied. Other variations on data stored may also be accommodated in the general method of operation.

It will be understood that the adjunct arrhythmia detection criteria may be satisfied either before or after the rhythm is classified as polymorphic, and the therapy command may be delayed for a number of seconds in the former case to determine if the rhythm progresses from a monomorphic to a polymorphic classification. Conversely, at the onset of ventricular tachycardia, wave shapes may initially test as polymorphic and then settle into a monomorphic pattern that can be pace-terminated. Therefore, the progression of a short series of high rate beats may be monitored to determine the progression before the arrhythmia therapy is either prescribed or delivered in blocks 310 and 312. In this respect, a provisional determination may be made in block 308 and either changed or confirmed depending on the computation of a series of successive morphology indices in block 304 and the results of the comparison in block 308. Naturally, the series would be selected to be relatively short, since the progression to a life threatening arrhythmia such as ventricular fibrillation may be quite rapid as indicated in the literature. And, the therapies would only be delivered in blocks 310 and 312 as long as the other adjunct criteria remain satisfied. In modem implantable pacemaker/cardioverter/defibrillators, the particular therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Therapies for fast ventricular tachycardia may be of the same general types provided in conjunction with detection of ventricular tachycardia at 616 (FIG. 8), and may include anti-tachycardia pacing and cardioversion pulse therapies. However, the therapy menu for fast ventricular tachycardia will be more aggressive than the therapy set for slower ventricular tachycardias. For example, fewer or no attempts at anti-tachycardia pacing may be undertaken prior to delivery of cardioversion pulses. Higher amplitude cardioversion pulses may be specified.

Prior art patents illustrating such pre-set therapy menus of anti-tachyarrhythmia therapies include the above-cited '006, '380 and '970 patents. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

The references cited above in conjunction with descriptions of prior art tachycardia detection and treatment therapies are applicable here as well. Again, the focus of the present invention is to distinguish fibrillation from tachycardias. It is believed that in the context of practicable devices, the physician will be provided with the ability to select which of a number of available therapies are provided in response to the detection of slow or fast tachycardias.

In the event that an aggressive therapy is commanded at step 318, the typical therapy will be delivery of a high amplitude defibrillation pulse, typically in excess of 10 joules, and in some cases as much as 35 joules or more. As in the case of currently available implantable pacemaker/cardioverter/defibrillators, and as discussed in the above-cited references, it is envisioned that the amplitude of the defibrillation pulse may be incremented in response to failure of an initial pulse or pulses to terminate fibrillation.

After delivery of a tachycardia therapy at step 316 or 318, the adjunct arrhythmia detection criteria are again monitored as the morphology of post-therapy wave shapes is again derived. The microprocessor updates the tachyarrhythmia detection methodologies. As discussed in the above-cited patents, in some cases it is desirable to have a different standard for re-detection of a tachyarrhythmia than for initial detection of the tachyarrhythmia. Typically the criteria for re-detection will be less stringent than for initial detection, and, in the present invention, the threshold index value may be reduced. Similarly, the microprocessor updates the therapy schedule, to reflect that the previously scheduled therapy had been delivered. As discussed above, in current implantable pacemaker/cardioverter/defibrillators, this generally results in the delivery of a more aggressive therapy upon re-detection of tachycardia. After updating the tachyarrhythmia related functions, the microprocessor returns the device to VVI mode bradycardia pacing and awaits the next R-wave sense event interrupt.

If a tachyarrhythmia was detected previously, the microprocessor checks to determine whether a series of R—R intervals, including the most recent, indicates a return to sinus rhythm or termination of a previously detected arrhythmia. The criterion of detection of return to sinus rhythm may be a series of a predetermined number of sequential R—R intervals which are greater than the tachycardia detection interval (TDI), for example. Following termination detection, the counters, detection methodologies and therapy schedules are all appropriately updated, and the device returns to VVI mode pacing, as discussed above.

The VT/VF discriminator provided by the present invention is readily implementable into pacemaker/cardioverter/defibrillators of any of the known types and in future such devices. The use of the sense event detection of the R-wave or P-wave as the fiducial point simplifies the system and allows a simple way of aligning the windowed wave shape data sets. The simple fiducial point designation and mathematical comparison and addition steps avoid the difficulties inherent in correlation algorithms employed in the prior art, while providing the benefits thereof. The broad applicability of the discriminator in the present application is believed to be one of its most valuable attributes.

Furthermore, it should be recognized that although the disclosed embodiment deals with fibrillation and tachycardia in the lower chambers or ventricles of the heart, the invention may be usefully practiced in the context of the upper chambers or atria of the heart, which are also prone to tachycardia and fibrillation in some patients.

In addition, while the therapies discussed in conjunction with the disclosed embodiment generally relate to delivery of electrical pulses, it should be understood that the invention may be usefully practiced in conjunction with any device adapted to deliver differing therapies for tachycardia and fibrillation, including drug therapies, non-pulsatile electrical therapies, and any other such therapies as may be implemented in such devices as their development progresses, whether applied directly to the heart or systemically.

Similarly, it should be understood that the discriminator of the present invention, while particularly adapted for use in or in conjunction with an implantable cardioverter/defibrillator may also in some cases be usefully practiced in conjunction with a non-implantable device, in a device which, for example only treats fibrillation or only treats tachycardia, or even in a device adapted primarily for diagnostic purposes.

In conjunction with above application, I claim:

1. In a cardioverter/defibrillator of the type comprising treatment means for delivering a first therapy to a patient's heart to treat tachycardia and a second therapy to said patient's heart to treat fibrillation in response to criteria for discriminating tachycardia from fibrillation, a method of assisting the discrimination between tachycardia and fibrillation through a comparison of the degree of morphology of a series of cardiac electrical signals associated with cardiac depolarizations comprising the steps of:

sensing electrical signals from said patient's heart accompanying the depolarization of a chamber or chambers of said patient's heart as the electrical signals successively appear;

successively sampling, processing and temporarily storing the sensed electrical signals as sets of wave shape amplitude data values of the sensed electrical signals;

successively determining the sampled point at which the sensed electrical signal meets predetermined sense detect criteria and for issuing a fiducial point signal indicative thereof;

successively selecting sub-sets of the sets of the processed and stored wave shape data referenced to the fiducial point signal, the sub-sets of wave shape data of a series of data sets being consistently selected with respect to the fiducial point signal so the selected sub-sets of data are consistent in number and sample point position with respect to each fiducial point signal;

successively positionally aligning the fiducial point signals of a series of subsets of wave shape data to positionally align the series of wave shape sub-set data;

first, comparing the values of the aligned data of at least two successive selected sub-sets of the processed and stored wave shape data to derive a like numbered sub-set of morphology difference data;

summing the sub-set of morphology difference data to provide a sampled morphology index value;

providing a threshold morphology index value which, if exceeded is indicative of the onset of polymorphic cardiac rhythm indicative of fibrillation; and second, comparing the sampled morphology index value to the threshold morphology index value and generating a tachycardia or a fibrillation discrimination signal for use in confirming tachycardia or fibrillation and for selecting the appropriate therapy.

2. The method of claim 1 wherein:

the step of sensing electrical signals from said patient's heart accompanying the depolarization of a chamber or chambers of said patient's heart as the electrical signals successively appear further comprises:

providing a pair of widely spaced sense electrodes in relation to the heart and a first sense amplifier coupled to the widely spaced sense electrodes to detect the far field electrical signals accompanying depolarization of the heart; and the steps of successively determining the sample point at which the sensed electrical signal meets predetermined sense detect criteria and for issuing a fiducial point signal indicative thereof further comprises:

providing a pair of closely spaced sense electrodes in relation to the heart and a second sense amplifier coupled to the closely spaced sense electrodes to detect the near field electrical signals accompanying depolarization of the heart; and sampling the value of the near field electrical signals and issuing the fiducial point signal when a sampled value meets the predetermined sense detect criteria.

3. The method of claim 2 wherein the second comparing step further comprises:

measuring the cumulative variability of a series of sampled morphology index values of a series of depolarizations of said chamber or chambers of said patient's heart and for providing a further tachycardia or fibrillation discrimination signal for selecting between the appropriate therapies as a function of said measured variability.

4. The method of claim 3 wherein the second comparing step further comprises:

comparing the sampled morphology index value to the threshold morphology index value and generating a tachycardia or a fibrillation count signal for a series of sampled morphology index values;

counting the relative numbers of fibrillation and tachycardia count signals in the series, whereby a progression from a monomorphic tachycardia to a polymorphic fibrillation may be confirmed; and providing the tachycardia or fibrillation discrimination signal for selecting between the appropriate therapies as a function of the count.

5. The method of claim 4 wherein the first comparing step further comprises:

periodically selecting and storing a reference sub-set of processed and stored wave shape data having a sampled morphology index value confirmed as indicating tachycardia; comparing the values of the aligned data of a succeeding series of selected subsets of the processed and stored wave shape data to the reference subset to derive the like numbered sub-set of morphology difference data in each case; and after the series of comparing steps, selecting and storing an updated reference sub-set of processed and stored data having a sampled morphology index value confirmed as indicating tachycardia, if any.

6. The method of claim 5 wherein the first comparing step further comprises:

adjusting the number of the series of comparing steps between the selection and storage of the updated reference sub-set as a function of rate or stability of a series of depolarizations of said chamber or chambers of said patient's heart.

7. The method of claim 1 wherein the second comparing step further comprises:

measuring the cumulative variability of a series of sampled morphology index values of a series of depolarizations of said chamber or chambers of said patient's heart and for providing a further tachycardia or fibrillation discrimination signal for selecting between the appropriate therapies as a function of said measured variability.

8. The method of claim 7 wherein the second comparing step further comprises:

comparing the sampled morphology index value to the threshold morphology index value and generating a tachycardia or a fibrillation count signal for a series of sampled morphology index values;

counting the relative numbers of fibrillation and tachycardia count signals in the series, whereby a progression from a monomorphic tachycardia to a polymorphic fibrillation may be confirmed; and providing the tachycardia or fibrillation discrimination signal for selecting between the appropriate therapies as a function of the count.

9. The method of claim 8 wherein the first comparing step further comprises:

periodically selecting and storing a reference sub-set of processed and stored wave shape data having a sampled morphology index value confirmed as indicating tachycardia; comparing the values of the aligned data of a succeeding series of selected subsets of the processed and stored wave shape data to the reference sub-set to derive the like numbered sub-set of morphology difference data in each case; and after the series of comparing steps, selecting and storing an updated reference sub-set of processed and stored data having a sampled morphology index value confirmed as indicating tachycardia, if any.

10. The method of claim 9 wherein the first comparing step further comprises:

adjusting the number of the series of comparing steps between the selection and storage of the updated reference sub-set as a function of rate or stability of a series of depolarizations of said chamber or chambers of said patient's heart.

11. The method of claim 1 wherein the second comparing step further comprises:

comparing the sampled morphology index value to the threshold morphology index value and generating a tachycardia or a fibrillation count signal for a series of sampled morphology index values;

counting the relative numbers of fibrillation and tachycardia count signals in the series, whereby a progression from a monomorphic tachycardia to a polymorphic fibrillation may be confirmed; and providing the tachycardia or fibrillation discrimination signal for selecting between the appropriate therapies as a function of the count.

12. The method of claim 11 wherein the first comparing step further comprises:

periodically selecting and storing a reference sub-set of processed and stored wave shape data having a sampled morphology index value confirmed as indicating tachycardia; comparing the values of the aligned data of a succeeding series of selected subsets of the processed and stored wave shape data to the reference sub- set to derive the like numbered sub-set of morphology difference data in each case; and after the series of comparing steps, selecting and storing an updated reference sub-set of processed and stored data having a sampled morphology index value confirmed as indicating tachycardia, if any.

13. The method of claim 12 wherein the first comparing step further comprises:

adjusting the number of the series of comparing steps between the selection and storage of the updated reference sub-set as a function of rate or stability of a series of depolarizations of said chamber or chambers of said patient's heart.

14. The method of claim 1 wherein the first comparing step further comprises:

periodically selecting and storing a reference sub-set of processed and stored wave shape data having a sampled morphology index value confirmed as indicating tachycardia; comparing the values of the aligned data of a succeeding series of selected subsets of the processed and stored wave shape data to the reference subset to derive the like numbered sub-set of morphology difference data in each case; and after the series of comparing steps, selecting and storing an updated reference sub-set of processed and stored data having a sampled morphology index value confirmed as indicating tachycardia, if any.

15. The method of claim 14 wherein the first comparing step further comprises:

adjusting the number of the series of comparing steps between the selection and storage of the updated reference sub-set as a function of rate or stability of a series of depolarizations of said chamber or chambers of said patient's heart.

16. In a cardioverter/defibrillator of the type comprising treatment means for delivering a first therapy to a patient's heart to treat tachycardia and a second therapy to said patient's heart to treat fibrillation in response to criteria for discriminating tachycardia from fibrillation, a apparatus for assisting the discrimination between tachycardia and fibrillation through a comparison of the degree of morphology of a series of cardiac electrical signals associated with cardiac depolarizations comprising:

means for sensing electrical signals from said patient's heart accompanying the depolarization of a chamber or chambers of said patient's heart as the electrical signals successively appear;

means for successively sampling, processing and temporarily storing the sensed electrical signals as sets of wave shape data representative of a like numbered set of wave shape amplitude values of the sensed electrical signals;

means for successively determining the sample point at which the sensed electrical signal meets predetermined sense detect criteria and for issuing a fiducial point signal indicative thereof;

means for successively selecting sub-sets of the sets of the processed and stored wave shape data referenced to the fiducial point signal, the sub-sets of wave shape data of a series of data sets being consistently selected with respect to the fiducial point signal so the selected sub-sets of data are consistent in number and sample point position with respect to each fiducial point signal;

means for successively positionally aligning the fiducial point signals of a series of sub-sets of wave shape data to positionally align the series of wave shape sub-set data;

first means for comparing the values of the aligned data of at least two successive selected sub-sets of the processed and stored wave shape data to derive a like numbered sub-set of morphology difference data;

means for summing the sub-set of morphology difference data to provide a sampled morphology index value; means for providing a threshold morphology index value which, if exceeded is indicative of the onset of polymorphic cardiac rhythm indicative of fibrillation; and second means for comparing the sampled morphology index value to the threshold morphology index value and generating a tachycardia or a fibrillation discrimination signal for use in confirming tachycardia or fibrillation and for selecting the appropriate therapy.

17. The apparatus of claim 16 wherein:

said means for sensing electrical signals from said patient's heart accompanying the depolarization of a chamber or chambers of said patient's heart as the electrical signals successively appear further comprises:

a pair of widely spaced sense electrodes adapted to be positioned in relation to the heart; and a first sense amplifier coupled to the widely spaced sense electrodes to detect the far field electrical signals accompanying depolarization of the heart; and said means for successively determining the sample point at which the sensed electrical signal meets predetermined sense detect criteria and for issuing a fiducial point signal indicative thereof further comprises:

a pair of closely spaced sense electrodes adapted to be positioned in relation to the heart; and a second sense amplifier coupled to the closely spaced sense electrodes to detect the near field electrical signals accompanying depolarization of the heart; and means for issuing the fiducial point signal when a value of the near field electrical signal meets the predetermined sense detect criteria.

18. The apparatus of claim 17 wherein said second comparing means further comprises:

means for measuring the cumulative variability of a series of sampled morphology index values of a series of depolarizations of said chamber or chambers of said patient's heart and for providing a further tachycardia or fibrillation discrimination signal for selecting between the appropriate therapies as a function of said measured variability.

19. The apparatus of claim 18 wherein said second comparing means further comprises:

means for comparing the sampled morphology index value to the threshold morphology index value and generating a tachycardia or a fibrillation count signal for a series of sampled morphology index values;

means for counting the relative numbers of fibrillation and tachycardia count signals in the series, whereby a progression from a monomorphic tachycardia to a polymorphic fibrillation may be confirmed; and means for providing the tachycardia or fibrillation discrimination signal for selecting between the appropriate therapies as a function of the count.

20. The apparatus of claim 19 wherein said first comparing means further comprises:

means for periodically selecting and storing a reference sub-set of processed and stored wave shape data having a sampled morphology index value confirmed as indicating tachycardia;

means for comparing the values of the aligned data of a succeeding series of selected sub-sets of the processed and stored wave shape data to the reference sub-set to derive the like numbered sub-set of morphology difference data in each case; and means for selecting and storing an updated reference sub-set of processed and stored data having a sampled morphology index value confirmed as indicating tachycardia, if any.

21. The apparatus of claim 20 wherein said first comparing means further comprises:

means for adjusting the number of the series of comparisons between the selection and storage of the updated reference sub-set as a function of rate or stability of a series of depolarizations of said chamber or chambers of said patient's heart.

22. The apparatus of claim 16 wherein said second comparing means further comprises:

means for measuring the cumulative variability of a series of sampled morphology index values of a series of depolarizations of said chamber or chambers of said patient's heart and for providing a further tachycardia or fibrillation discrimination signal for selecting between the appropriate therapies as a function of said measured variability.

23. The apparatus of claim 22 wherein said second comparing means further comprises:
   means for comparing the sampled morphology index value to the threshold morphology index value and generating a tachycardia or a fibrillation count signal for a series of sampled morphology index values;
   means for counting the relative numbers of fibrillation and tachycardia count signals in the series, whereby a progression from a monomorphic tachycardia to a polymorphic fibrillation may be confirmed; and
   means for providing the tachycardia or fibrillation discrimination signal for selecting between the appropriate therapies as a function of the count.

24. The apparatus of claim 23 wherein said first comparing means further comprises:
   means for periodically selecting and storing a reference sub-set of processed and stored wave shape data having a sampled morphology index value confirmed as indicating tachycardia;
   means for comparing the values of the aligned data of a succeeding series of selected sub-sets of the processed and stored wave shape data to the reference sub-set to derive the like numbered sub-set of morphology difference data in each case; and
   means for selecting and storing an updated reference sub-set of processed and stored data having a sampled morphology index value confirmed as indicating tachycardia, if any.

25. The apparatus of claim 24 wherein said first comparing means further comprises:
   means for adjusting the number of the series of comparing steps between the selection and storage of the updated reference sub-set as a function of rate or stability of a series of depolarizations of said chamber or chambers of said patient's heart.

26. The apparatus of claim 16 wherein said second comparing means further comprises:
   means for comparing the sampled morphology index value to the threshold morphology index value and generating a tachycardia or a fibrillation count signal for a series of sampled morphology index values;
   means for counting the relative numbers of fibrillation and tachycardia count signals in the series, whereby a progression from a monomorphic tachycardia to a polymorphic fibrillation may be confirmed; and
   means for providing the tachycardia or fibrillation discrimination signal for selecting between the appropriate therapies as a function of the count.

27. The apparatus of claim 26 wherein said first comparing means further comprises:
   means for periodically selecting and storing a reference sub-set of processed and stored wave shape data having a sampled morphology index value confirmed as indicating tachycardia;
   means for comparing the values of the aligned data of a succeeding series of selected sub-sets of the processed and stored wave shape data to the reference sub-set to derive the like numbered sub-set of morphology difference data in each case; and
   means for selecting and storing an updated reference sub-set of processed and stored data having a sampled morphology index value confirmed as indicating tachycardia, if any.

28. The apparatus of claim 27 wherein said first comparing means further comprises:
   means for adjusting the number of the series of comparing steps between the selection and storage of the updated reference sub-set as a function of rate or stability of a series of depolarizations of said chamber or chambers of said patient's heart.

29. The apparatus of claim 16 wherein said first comparing means further comprises:
   means for periodically selecting and storing a reference sub-set of processed and stored wave shape data having a sampled morphology index value confirmed as indicating tachycardia;
   means for comparing the values of the aligned data of a succeeding series of selected sub-sets of the processed and stored wave shape data to the reference sub-set to derive the like numbered sub-set of morphology difference data in each case; and
   means for selecting and storing an updated reference sub-set of processed and stored data having a sampled morphology index value confirmed as indicating tachycardia, if any.

30. The apparatus of claim 29 wherein said first comparing means further comprises:
   means for adjusting the number of the series of comparing steps between the selection and storage of the updated reference sub-set as a function of rate or stability of a series of depolarizations of said chamber or chambers of said patient's heart.

31. In a cardioverter/defibrillator of the type comprising treatment means for delivering a first therapy to a patient's heart to treat a monomorphic arrhythmia and a second therapy to said patient's heart to treat a polymorphic arrhythmia in response to criteria for discriminating therebetween, a method of assisting the discrimination through a comparison of the degree of morphology of the far field electrogram associated with cardiac depolarizations recurring at a tachycardia rate comprising the steps of:
   providing a first pair of closely spaced electrodes in or adjacent to a chamber of a heart from which a near field electrogram may be detected;
   providing a second pair of widely spaced electrodes in or adjacent to a chamber of a heart from which a far field electrogram may be detected;
   sensing the near field waveform of the electrogram successively appearing across the first pair of electrodes and successively determining a fiducial point at which the sensed waveform amplitude value meets predetermined sense detect criteria and issuing a fiducial point signal indicative thereof;
   sensing the far field waveform of the electrogram successively appearing across the second pair of electrodes and providing a set of far field sampled amplitude data;
   aligning successive sets of far field sampled amplitude data positionally aligned to the near field fiducial point of each such data set;
   processing the values of the aligned successive sets of data to provide a sampled morphology index value; and generating a tachycardia or a fibrillation discrimination signal as a function of the sampled morphology index value for use in confirming monomorphic tachycardia or polymorphic tachycardia or fibrillation and for selecting the appropriate therapy.

32. The method of claim 31 wherein the generating step further comprises:
providing a threshold morphology index value which, if exceeded is indicative of the onset of polymorphic cardiac rhythm; and
comparing the sampled morphology index value to the threshold morphology index value and generating a polymorphic or a monomorphic discrimination signal for use in confirming the nature of the arrhythmia and for selecting the appropriate therapy.

33. The method of claim 32 wherein the processing step further comprises:
establishing event data windows in alignment with and extending for predetermined time windows with respect to each detected fiducial point;
comparing sub-sets of the far field sampled amplitude data values of the aligned successive sets of data falling within the event data windows to develop a subset of sampled amplitude difference data values; and
summing the sampled amplitude difference data values to derive the sampled morphology index value.

34. The method of claim 31 wherein the processing step further comprises:
establishing event data windows in alignment with and extending for predetermined time windows with respect to each detected fiducial point;
comparing sub-sets of the far field sampled amplitude data values of the aligned successive sets of data falling within the event data windows to develop a subset of sampled amplitude difference data values; and
summing the sampled amplitude difference data values to derive the sampled morphology index value.

35. The method of claim 31 wherein the comparing step further comprises:
measuring the cumulative variability of a series of sampled morphology index values of a series of depolarizations of said chamber or chambers of said patient's heart and providing a further morphology discrimination signal for selecting between the appropriate therapies as a function of said measured variability.

36. The method of claim 31 wherein the comparing step further comprises:
comparing the sampled morphology index value to the threshold morphology index value and generating a monomorphic or polymorphic count signal for a series of sampled morphology index values;
counting the relative numbers of fibrillation and tachycardia count signals in the series, whereby a progression from a monomorphic tachycardia to a polymorphic fibrillation may be confirmed; and
providing the tachycardia or fibrillation discrimination signal for selecting between the appropriate therapies as a function of the count.

37. The method of claim 31 wherein the processing step further comprises:
periodically selecting and storing a reference sub-set of processed and stored wave shape data having a sampled morphology index value confirmed as indicating mono-morphology;
comparing the values of the aligned data of a succeeding series of selected subsets of the processed and stored wave shape data to the reference sub-set to derive the like numbered sub-set of morphology difference data in each case; and
after the series of comparing steps, selecting and storing an updated reference sub-set of processed and stored data having a sampled morphology index value confirmed as indicating mono-morphology, if any.

38. In a cardioverter/defibrillator of the type comprising treatment means for delivering a first therapy to a patient's heart to treat a monomorphic arrhythmia and a second therapy to said patient's heart to treat polymorphic arrhythmia in response to criteria for discriminating therebetween, apparatus for assisting the discrimination through a comparison of the degree of morphology of a series of cardiac electrical signals associated with cardiac depolarizations recurring at a tachycardia rate comprising:
means for sensing near field and far field electrical signals from said patient's heart accompanying the depolarization of a chamber or chambers of said patient's heart as the electrical signals successively appear;
means for sampling the far field electrical signals and for providing sets of waveform data representative of a like numbered set of wave shape amplitude values of the sensed far field electrical signals;
means for successively determining a fiducial point at which the sensed near field electrical signal amplitude values meets predetermined sense detect criteria and for issuing a fiducial point signal indicative thereof;
means for aligning successive sets of far field wave shape data positionally aligned with the fiducial point of each corresponding near field electrical signal;
means for processing the values of the aligned data of at least two selected sub-sets of the stored far field wave shape data to provide a sampled morphology index value;
means for providing a threshold morphology index value which, if exceeded is indicative of the onset of polymorphic cardiac rhythm indicative of fibrillation; and
means for comparing the sampled morphology index value to the threshold morphology index value and generating a morphology discrimination signal for use in confirming monomorphic tachycardia or polymorphic tachycardia or fibrillation and for selecting the appropriate therapy.

39. The apparatus of claim 38 wherein:
said sensing means for sensing electrical signals from said patient's heart accompanying the depolarization of a chamber or chambers of said patient's heart as the electrical signals successively appear further comprises:
a pair of widely spaced sense electrodes adapted to be positioned in relation to the heart; and
a first sense amplifier coupled to the widely spaced sense electrodes to detect the far field electrical signals accompanying depolarization of the heart; and
said means for successively determining the fiducial point further comprises:
a pair of closely spaced sense electrodes adapted to be positioned in relation to the heart; and
a second sense amplifier coupled to the closely spaced sense electrodes to detect the near field electrical signals accompanying depolarization of the heart; and means for issuing the fiducial point signal when a value of the near field electrical signal meets the predetermined sense detect criteria.

40. The apparatus of claim 38 wherein said comparing means further comprises:

means for measuring the cumulative variability of a series of sampled morphology index values of a series of depolarizations of said chamber or chambers of said patient's heart and for providing a further morphology discrimination signal for selecting between the appropriate therapies as a function of said measured variability.

41. The apparatus of claim 38 wherein said comparing means further comprises:

means for comparing the sampled morphology index value to the threshold morphology index value and generating a monomorphic or a polymorphic count signal for a series of sampled morphology index values;

means for counting the relative numbers of monomorphic and polymorphic count signals in the series, whereby a progression from a monomorphic tachycardia to a polymorphic tachycardia or fibrillation may be confirmed; and means responsive to the counted number for selecting between the appropriate therapies as a function of the count.

42. The apparatus of claim 38 wherein said processing means further comprises:

means for periodically selecting and storing a reference sub-set of processed and stored wave shape data having a sampled morphology index value confirmed as indicating tachycardia;

means for comparing the values of the aligned data of a succeeding series of selected sub-sets of the processed and stored wave shape data to the reference sub-set to derive the like numbered sub-set of morphology difference data in each case; and means for selecting and storing an updated reference sub-set of processed and stored data having a sampled morphology index value confirmed as indicating tachycardia, if any.

43. The apparatus of claim 42 wherein said comparing means further comprises:

means for adjusting the number of the series of comparisons between the selection and storage of the updated reference sub-set as a function of rate or stability of a series of depolarizations of said chamber or chambers of said patient's heart.

* * * * *